United States Patent [19]

Gallaher

[11] Patent Number: 4,880,779

[45] Date of Patent: Nov. 14, 1989

[54] METHOD OF PREVENTION OR TREATMENT OF AIDS BY INHIBITION OF HUMAN IMMUNODEFICIENCY VIRUS

[75] Inventor: William R. Gallaher, New Orleans, La.

[73] Assignee: Research Corporation Technologies, Inc., Tucson, Ariz.

[21] Appl. No.: 80,529

[22] Filed: Jul. 31, 1987

[51] Int. Cl.$^4$ ...................... A61K 37/02; A61K 39/21
[52] U.S. Cl. ........................................ 514/15; 514/16; 514/17; 514/18; 530/327; 530/328; 530/329; 530/330; 530/331
[58] Field of Search ............... 530/327, 328, 329, 330, 530/331; 514/15, 16, 17, 18

[56] References Cited

U.S. PATENT DOCUMENTS 4,751,216 6/1988 Gottlieb .............................. 514/18

FOREIGN PATENT DOCUMENTS 0225066 6/1987 European Pat. Off. .

OTHER PUBLICATIONS

Miyoshi et al., "Structure-Taste Relationship of Novel α-L-Aspartyl Dideptide Sweetners", *Bull. Chem. Soc. Japan*, vol. 51 (5) 1433-1440, (1978).

*Primary Examiner*—John Kight
*Assistant Examiner*—Nathan M. Nutter
*Attorney, Agent, or Firm*—Scully, Scott, Murphy & Presser

[57] ABSTRACT

The present invention relates to a method of prevention or treatment of AIDS by inhibition of the human immunodeficiency virus (HIV). Inhibition of the virus is achieved by administration of an inhibitory peptide containing the sequence Phe-X-Gly, wherein X is an amino acid.

13 Claims, 2 Drawing Sheets

A.
B.
C.

D. 0.9mM
E. 0.3mM
F. 0.1mM

METHOD OF PREVENTION OR TREATMENT OF AIDS BY INHIBITION OF HUMAN IMMUNODEFICIENCY VIRUS

FIELD OF THE INVENTION

The present invention relates to a method of prevention or treatment of acquired immune deficiency syndrome (AIDS). More specifically, the invention relates to a method of inhibiting infection by the viral etiologic agent of AIDS through administration of an inhibitory peptide.

BACKGROUND OF THE INVENTION

A wide variety of different types of viruses are well-known as being the etiologic agents for a number of diseases in both animals and man. Because of the large number of potentially widespread epidemics, e.g. influenza, herpes, and AIDS, to name but a few, methods are constantly being sought for either prevention or cure of the diseases caused by these entities. This effort has been hampered to a large extent by the unusual structural and functional aspects of viruses, which are quite unlike any other known infectious agents, such as bacteria or fungi. The virus itself consists essentially of nucleic acid surrounded by a lipid-protein envelope; the virus does not replicate in the host by simple division like a bacterium, but rather multiplies by invading a host cell and, by virture of the action of the viral nucleic acid, reprogramming the cell to synthesize the viral components. The extensive use of mimicry of cellular mechanisms by the virus makes it especially difficult to generate drugs which are selectively toxic to viral infection.

In more recent years, an increased understanding of the structure, and related function of different viruses has provided an insight into the detailed mechanisms by which a viral particle invades a cell. The protein elements of the envelope, which generally consist of matrix proteins and glycoproteins, may play an integral role in the infection process. In fact it is now known that the glycoprotein components of the envelopes of many viruses are absolutely critical to the successful entry of the virus into the host cell. For example, in a large number of essentially unrelated types of virus, such as paramyxoviruses, influenza viruses and retroviruses, a common pattern exists. Attachment or adsorption of the virus to the host cell membrane is achieved by the interaction of an "attachment" or "receptor-binding" viral glycoprotein with a specific receptor on the host cell surface. Following attachment of the virus, fusion of the target cell membrane with the viral envelope occurs via the mediation of a fusion glycoprotein of the virus, which probably penetrates the host cell at a particular site, and then may shorten, drawing the two entities in closer proximity. Once fusion occurs, the cytoplasm of the cell is merged with the contents of the virus and the viral nucleic acid may then begin to direct the cell machinery.

This knowledge of the mechanism of cell invasion by the virus provides a possible key to development of methods of prevention of penetration. It is theoretically possible to attempt to disrupt the process, at any one of the aforementioned steps and therefore prevent the virus from gaining access to the inside of the cell. One way in which this can be done is by blocking the receptor sites of the glycoprotein or otherwise preventing one or both from carrying out the attachment and/or fusion process. This in fact has been achieved in paramyxoviruses, by application of of small peptide, Phe-X-Gly; which mimics the critical binding function of the fusion peptide (Richardson, et al., *Virology* 105:202–222, 1980; Varsanyi, et al., *Virology* 147: 110–117, 1985). The peptide homologue somehow interferes with the normal function of the fusion protein, thereby preventing fusion and subsequent infection of the cell by the virus. Although a promising indication, however, there is typically no possibility of extrapolating treatment for one type of virus to other unrelated types: each family of viruses typically is characterized by its own particular glycoproteins, each having a specific length and amino acid sequence; these may, in fact, vary to some extent even within families, or among variants in a "genus." Structural homologues between unrelated or distantly related virus groups are very uncommon. It is this variability in envelope structure, in addition to potential variables in type and arrangement of nucleic acid, which makes successful treatment of viral disease so unpredictable, and also explains the unavailability of broad spectrum antiviral agent. Thus, each group of viruses must be treated separately when considering possible therapeutic regimens.

In this vein, the viral disease currently presenting the greatest concern to the human population is acquired immune deficiency syndrom (AIDS). Now reaching nearly epidemic proportions, the disease has to date evaded all attempts to contrtol or cure it. Relatively little is known about the causative agent, variously referred to as HTLV-III, LAV or HIV (usually HIV-1). It is known to be a retrovirus, a group of viruses characterized by the presence of a single-stranded RNA and reverse transcriptase in the virion. Among the other retroviruses are many oncogenic viruses which induce sarcomas, leukemias, lymphomas, and mammary carcinomas. The AIDS virus, and other retroviruses appear to infect cells by the same attachment-fusion process described above. The product of the env gene of HIV, which codes for the envelope glycoprotein of the virus is apparently unique, and shows no significant homology with any known protein (Wain-Hobson et al., *Cell* 40: 9–17, 1985). The sequence of the HIV envelope glycoprotein has been described by Muesing et al. (*Nature* 313:456–458, 1985). However, even with this knowledge of the structure of the env product, there has been, to date, only limited success in exploiting this information for the production of inhibitory compounds. An octapeptide, Peptide T, has been synthesized based on homology to a sequence in gp120, the attachment glycoprotein, which is purported to inhibit binding of HIV to susceptible cells. The sequence is Ala-Ser-Thr-Thr-Thr-Asn-Tyr-Thr (Pert, et al., *PNAS USA* 83:9254–9258, 1986). The proposed utility of this peptide has caused much controversy. (*Science* 237:128–130, 1987).

It has now been unexpectedly discovered that a short sequence, Phe-Leu-Gly-Phe-Leu-Gly, within the fusion glycoprotein (gp41 in HIV, a cleavage product of the larger envelope glycoprotein gp160) of all retroviruses studied, including HIV, is highly conserved and appears to represent the critical region of the molecule for fusion purposes. Even more surprisingly, this sequence is found to some extent to correspond to similiar sequences in fusion glycoproteins of paramyxoviruses, although the remainder of the glycoprotein molecule sequences are quite dissimiliar between the two groups.

Examples of sequences of a number of retroviruses and paramyxoviruses is shown in Table 1 on next page. More importantly, however, it has further been determined that small peptides containing this tripeptide sequence or homologues thereof are capable of inhibiting the fusion process of the AIDS virus and other retroviruses, and thus provides a useful form of therapy and prophylaxis for individuals exposed to retrovirus, particularly HIV-1 infection.

TABLE 1

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| MSLS | . | . | . | . | . | . | . | . | . | . | Phe | Ala | Gly | Val | Ile | Leu | Ala | Gly | Ala | Ala | Leu | Gyl | Val | Ala | Thr | Ala | Ala |
| ReSV | Arg | Arg | . | . | . | . | . | . | . | . | Phe | Leu | Gly | Phe | Leu | Leu | Gly | Val | Gly | Ser | Ala | Ile | Ala | Ser | Gly | Val | Ala |
| HIV-1 | Lys | Arg | Ala | Val | Gly | . | Ile | Gly | Ala | Leu | Phe | Leu | Gly | Phe | Leu | Gly | Ala | Ala | Gly | Ser | Thr | Met | Gly | Ala | Arg | Ser | Met |
| | Lys | Arg | Ala | Val | Gly | Ala | Ile | Gly | Ala | Met | Phe | Leu | Gly | Phe | Leu | Gly | Ala | Ala | Gly | Ser | Thr | Met | Gly | Ala | Ala | Ser | Leu |
| | Lys | Arg | Ala | Ile | Gly | . | Leu | Gly | Ala | Met | Phe | Leu | Gly | Phe | Leu | Gly | Ala | Ala | Gly | Ser | Thr | Met | Gly | Ala | Ala | Ser | Leu |
| HIV-2 | Thr | Arg | Gly | Val | Phe | Val | Leu | Gly | . | . | Phe | Leu | Gly | Phe | Leu | Ala | Thr | Ala | Gly | Ser | Ala | Val | Gly | Ala | Ala | Ser | Leu |
| STLV-3 | Lys | Arg | Gly | Val | Phe | Val | Leu | Gly | . | . | Phe | Leu | Gly | Phe | Leu | Ala | Thr | Ala | Gly | Ser | Ala | Ile | Gly | Ala | Ala | Ser | Val |
| Viana | Lys | Arg | Gly | Ile | Gly | Leu | Val | . | . | Ile | Val | Leu | Ala | Ile | Met | Ala | Ile | Ile | . | Ala | Ala | . | . | Gly | . | Ala | Gly |
| SRV-1 | Lys | Arg | Ala | Ile | Glu | Phe | Ile | . | Pro | Leu | Val | Ile | Gly | . | Leu | Gly | Ile | Thr | Thr | Ala | Val | Ser | Thr | Gly | Thr | Ala | Gly |

Comparison of amino acid sequences of the fusion glycoproteins of a number of retroviruses [(HIV-1, HIV-2, Simian T-Cell lymphotrophic virus (STLV), Visra virus, and simian retrovirus (SRV-1)], and two paramyxoviruses [measles (MSLS) and respiratory syncytral virus [(ResV)].

BRIEF DESCRIPTION OF THE INVENTION

The present invention relates to a method of inhibition of retroviral infection which comprises administering to a host an inhibitory effective amount of a peptide comprising an active sequence Phe-X-Gly or Gly-X-Phe, wherein X is any amino acid. Preferably, X is a hydrophobic or neutral amino acid.

As used throughout the specification and claims, the word "inhibiting" with respect to the activity of the therapeutic peptides is to be understood as meaning inhibition both in a prophylactic sense, i.e., prevention of the initial transmission of the virus to an individual, as well as in the sense of preventing the infection from becoming established or ameliorating its effects, once the virus has been introduced into the body. Reference to AIDS virus is intended to encompass any human retrovirus associated with lymphadenopathy or immune deficiency syndrome as defined by the Center for Disease Control. Throughout the specification and claims, the abbreviation HIV (human immunodeficiency virus) will be used interchangeably with AIDS virus.

DETAILED DESCRIPTION OF THE INVENTION

Figure 1:
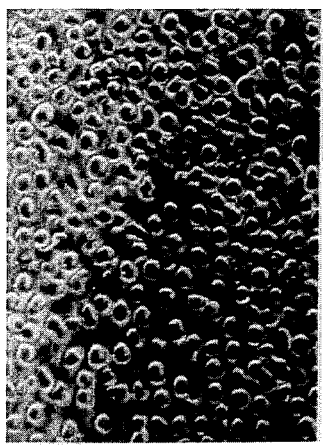
FIG. 1 shows phase photomicrographs comparing HIV infected cells which have been treated with inhibitory peptides, with infected, non-treated cells.
Figure 1:
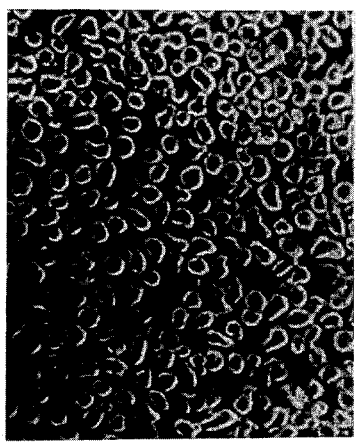
Figure 1:
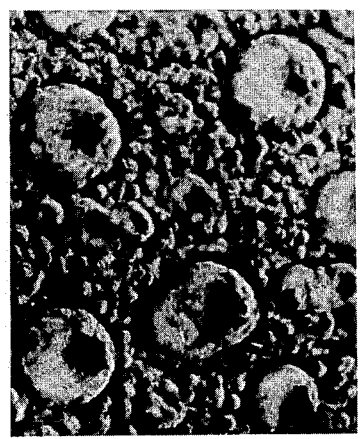
Figure 1:
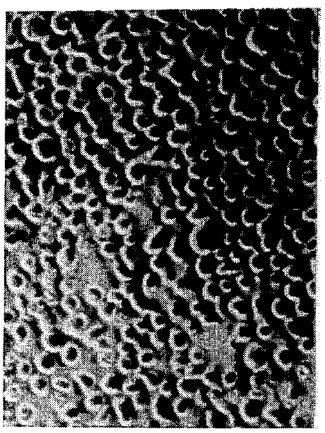
Figure 1:
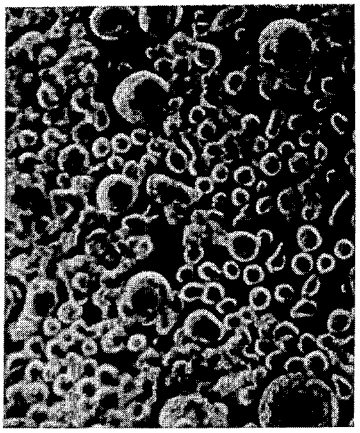
Figure 1:
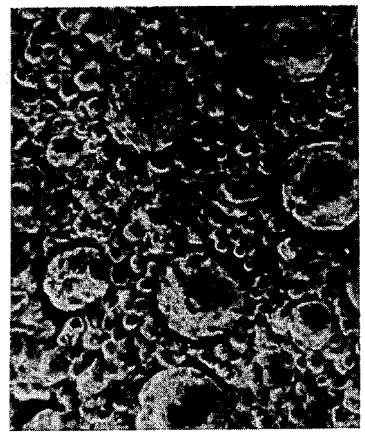

The present method employs analogues of a small portion of the natural fusion glycoprotein of a retrovirus in order to inhibit the normal fusion process of the virus in vivo. The tripeptide Phe-X-Gly or the inverse Gly-X-Phe, is the minimum sequence length required to achieve the necessary inhibition, but the addition of further amino acids at either the N- or C-terminus of the tripeptide does not affect the activity of the active portion of the peptide. Theoretically, there is no apparent limit to the number of additional amino acids, but in practical terms, the length of the therapeutic peptide sequence will be limited by commercial feasibility, as well as the increasing potential for allergenic or immunogenic reactions with longer peptides. Generally speaking, the preferred peptide will have no more than about 6–8 amino acids in addition to the critical Phe-X-Gly or Gly-X-Phe sequence. The arrangement of the amino acids outside the active sequence is not critical. If there are peptides both before and after the active sequence, it will be preferred to have not more than 2 before the Phe residue, and 3–4 after the glycine. The peptide may also be double ended, i.e., with the active sequence appearing at both ends, with intervening amino acids. The peptide may also consist of a tandem repeat, or inverse repeat of the active sequence.

The "X" amino acid may be any of the known amino acids, natural or synthetic. However, in a preferred embodiment, the X amino acid is a hydrophobic amino acid, such as the naturally occurring phenylalanine, tryptophan, tyrosine, or the synthetic naphthylalanine; or a neutral amino acid such as leucine, glycine, alanine, valine, or isoleucine. Particularly preferred are the sequences in which X is leucine, phenylalanine or glycine.

The identity of the additional amino acids, if present, is not particularly critical to the activity of the compound, and may be any of the known amino acids. Generally speaking, the addition of further residues to the critical tripeptide may be used to increase the solubility of the peptide as a whole. Also, in this regard, it is contemplated that the term "amino acid" as used herein refers to both the naturally occurring forms, as well as synthetic forms which have been modified by the additional side chains to increase solubility, biological half-life, or uptake and delivery to body tissues. Among such commonly used modifications are the addition of an N-carbobenzoxy, or O-sulfation. Such modification may also be used to increase the solubility of the peptides, and therefore facilitate this preparation of therapeutically useful compositions containing same. Both D- and L-forms of all amino acids are also contemplated. The active peptides may also be employed in the form of their pharmaceutically acceptable salts, particularly salts with various inorganic or organic bases. Among the salts which may be prepared are ammonium alkali metal salts; alkaline earth metal salts, and salts with organic bases such as dicyclohemamine.

The active peptides of the present invention are easily prepared by any of a wide range of known methods, (see, e.g., Jakubke et al., "Amino Acids, Peptides and Proteins", pp. 77–183, Wiley & Sons, 1977). Among the more commonly used techniques are coupling via the dicyclohexylcarbodiimide method or the solid phase Merrifield synthesis, in which a protected amino acid is bound to a resin particle as an ester bond. Amino acids having functional side chains such as tyrosine, are generally protected with an easily removed blocking group, which are well known to the skilled artisan. Any of the known techniques is equally suitable for the present purpose. Alternately, certain of the active peptides are available commercially.

The active peptides may be administered in a number of forms, to some extent depending upon the therapeutic intent. As noted above, one of the more useful aspects of the present method is its use prophylactically. In this regard, the peptides may be applied topically or transdermally, in the form of ointments, aqueous compositions, including solutions and suspensions, creams, lotions, aerosol sprays, or dusting powders. The peptides may also be pprpared and used in suppository form. The methods of preparation of such formulations is well known in the pharmaceutical art. Application of the therapeutic preparations may be to any area of the body which is likely to be a potential site of transmission of the virus, e.g., epidermally on cut or broken skin, vaginally, rectally or orally.

Alternately the peptides may be prepared for oral or parenteral administration. In oral administration capsules or tablets may be prepared in which the peptides are combined with stabilizers, excipients, carriers, preservatives or flavors, as is common in the pharmaceutical practice. For parenteral administration, i.e., intravenous, intramuscular, subcutaneous or intraperitoneal, the peptides are administered with a pharmaceutically acceptable carrier such as a sterile solution containing other solutes, for example, sufficient saline or glucose to make the solution isotonic.

The required dosage varies according to the mode of administration. For example for topical administration, a concentration in the composition of about 0.1–10 mM is sufficient. For oral or parenteral administration, the dosage range is typically about 0.001–1 mM. Modification of the dosage range may also be made depending on whether the peptides are to be used prophylactically, or for the purposes of inhibition of an established infection. Such modifications will be apparent to one skilled in the art. Although both these embodiments are contemplated for the present method, the use of the peptides for chemoprophylaxis is particularly advantageous. The peptides may also be used as a "morning after" remedy, i.e., a treatment initiated with 24 hours or so after suspected exposure to the virus.

Although the treatment of greatest interest is of course the AIDS virus, the utility of the present method is not so limited. The retrovirus group includes a substantial number of other pathogens, both human and animal, some of which are enumerated in Table 2. Therefore, the present method has both human and veterinary application.

TABLE 2

Examples of Known Retroviruses

Cisternavirus A
Mice, hamster, guinea pigs

Oncovirus B
Mammary carcinomas in mice — Mouse mammary tumor viruses: MMTV-S (Bittner's virus), MMTV-P (GR virus), MMTV-L Oncovirus C
Avian — Rous sarcoma virus (RSV)
Other chicken sarcoma viruses
Leukosis viruses (ALV)
Reticuloendotheliosis viruses
Pheasant viruses Mammalian — Murine sarcoma viruses (MSV)
Murine leukosis virus G (Gross or AKR virus)
Murine leukosis viruses (MLV)-F,M,R (Friend, Moloney, Rauscher viruses)
Murine radiation leukemia virus
Murine endogenous viruses
Rat leukosis virus
Feline leukosis viruses
Feline sarcoma virus
Feline endogenous virus (RD114)
Hamster leukosis virus (HLV)
Porcine leukosis virus
Bovine leukosis virus
Primate sarcoma viruses (woolly monkey; gibbon ape)
Primate sarcoma-associated virus
Primate endogenous viruses; baboon endogenous virus (BaEV), stumptail monkey virus, (MAC-1), owl monkey virus (OMC-1)

Reptilian — Viper virus

Oncovirus D
Primates — Mason-Pfizer monkey virus (MPMV)
Langur virus
Squirrel monkey virus Lentivirus E — Visna virus of sheep
Maedi virus Spumavirus F — Foamy viruses of primates, cats, humans and bovines The following example illustrates the effectiveness of the present peptides in inhibiting the fusion process of the viruses.

EXAMPLE 1

The commercially available peptides, carbobenzoxy-D- Phe-L-Phe-Gly (z-PPG) and Phe-Gly-Gly-Phe (PGGP) were obtained from Sigma Chemical Company, St. Louis, MO in granular form. Stock solutions were prepared to 20 mg/ml in dimethyl sulfoxide and stored at 0° C. A line of uninfected human lymphoblasts, RH9, and a line of lymphoblasts persistently infected with human immunodeficiency virus (HIV) were obtained from Dr. Robert Garry of Tulane Medical Center, New Orleans, La. and grown in RPMI medium containing 10% fetal calf serum obtained from Gibco, Grand Island, N.Y.

In the experimental protocol, RH9 cells are pretreated with various concentrations of either z-PPG or PGGP by adding a small aliquot of the peptide/DMSO solution to a suspension culture. After 1 hour, a suspension culture containing one-half the number of HIV-infected cells are added to the RH9-peptide mixture. The mixture is then incubated at 37° C. for 18 hours, and examined periodically for induction of cell fusion in the cell mixture.

Figure 2:
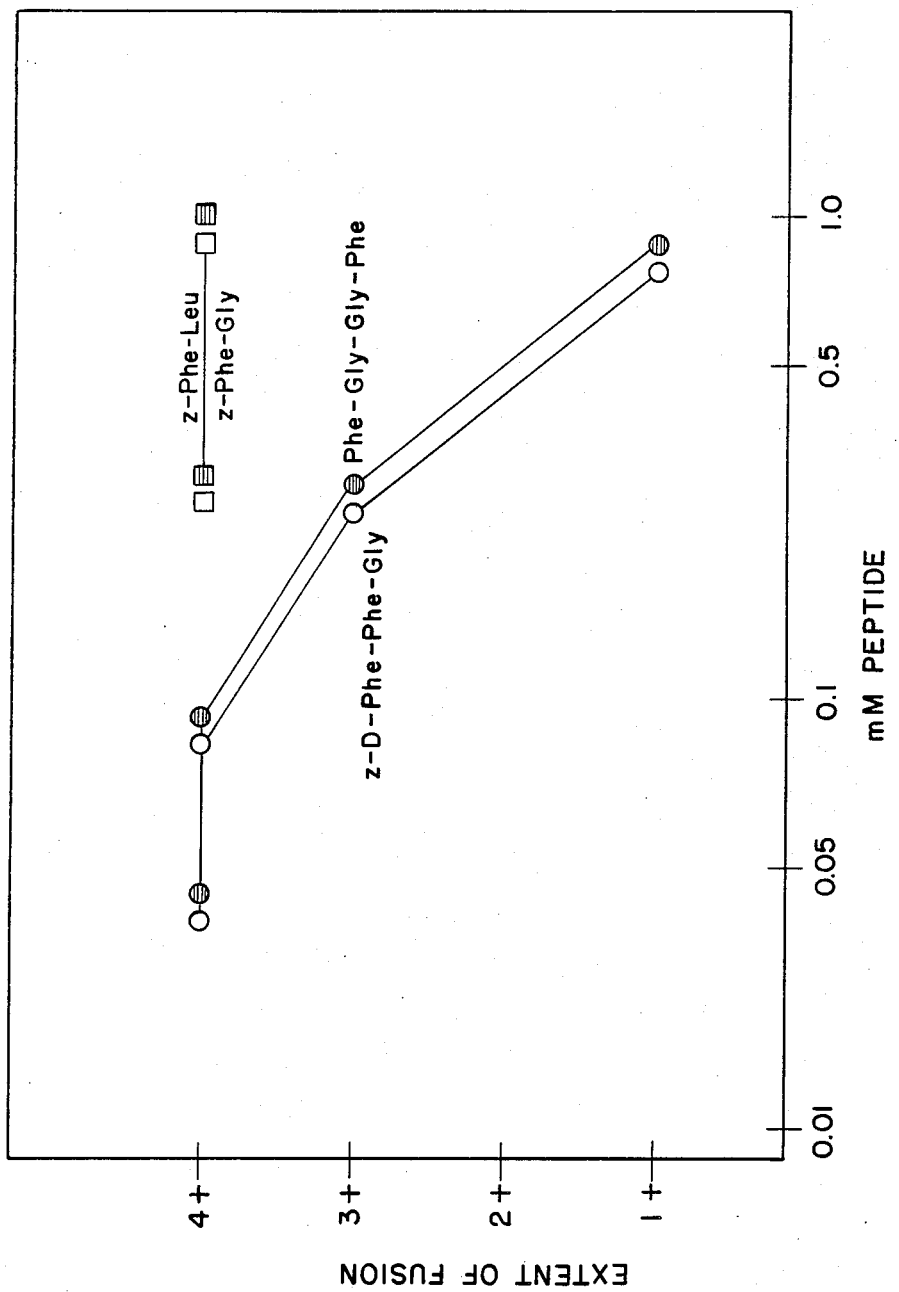
FIG. 2 graphically illustrates the relationship between concentration of inhibitory peptide, and the extent of fusion.

The results of such an experiment are shown in a series of phase photomicrographs in FIG. 1. Panel A shows a culture of uninfected RH9 cells, and panel B a culture of cells persistently infected with HIV, neither of which undergo cell fusion alone. Panel C shows the extensive cell fusion which occurs in the cell mixture in the absence of inhibitory peptides but in the presence or absence of up to 2% DMSO. A large number of polykaryocytes up to 7 times the normal cell diameter can be readily seen. Panels D, E, and F show the results of adding increasing dilutions of z-PPG in the range of 1.0–0.1 mM. These show almost complete inhibition of fusion at approximtely 1 mM, and a minimal inhibitory dose under these experimental conditions of 0.3 mM. Identical reults were obtained for PGGP, is indicated in FIG. 2, which shows the extent of fusion versus the concentration of peptide. Two other peptides, x-Phe-Leu and z-Phe-Gly, had no demonstrable activity. These data were also quantified by enumerating the polykaryocytes observed microscopically per unit area, and determining the average diameter of multinucleated cells. These data, shown in Table 3, confirm the visual and semi-quantitative observations, in that either peptide significantly inhibits both the number and size of polykaryocytes relative to untreated mixtures of infected and uninfected lymphoblasts.

The microscopic examinations showed no evidence of toxicity in the presence of these peptides. To test this further incubated cultures of either uninfected RH9 cells, or HIV-infected carrier cultures, were incubated with PGGP for four days. As shown in Table 4, there was no significant effect either on the rate of growth, final cell density or cell viability as a result of extended incubation in the presence of the peptide.

The Phe-X-Gly sequence is equally effective either in the presence or absence of an N-carbobenzoxy addition, and regardless of whether another amino acid is added to the peptide. Shorter peptides such as z-Phe-Leu are ineffective, we conclude that the critical functional group analogous to the viral fusion peptide sequence is Phe-X-Gly.

These results show a selective antiviral activity for peptides containing the Phe-X-Gly fusion peptide sequence which may be developed for either the prevention or treatment of infection by HIV or other viruses which share a common pathway of virus entry and/or fusion.

TABLE 3

Effect of Fusion Peptide Analogs on HIV-Induced Cell Fusion

| | | Polykaryocytes Per mm$^2$ | Polykaryocytes Mean Diameter (um) |
|---|---|---|---|
| RH9 only | | 4 | 29 |
| HIV RH9 only | | 8 | 27 |
| RH9 + HIV − RH9 | | 81 | 54 |
| | | 90 | 42 |
| PPG | 0.8 M | 4 | 26 |
| | 0.25 M | 59 | 37 |
| | 0.08 M | 105 | 51 |
| PGGP | 0.9 M | 5 | 26 |
| | 0.3 M | 61 | 32 |
| | 0.1 M | 31 | 42 |
| DMSO Control | | 135 | 48 |

TABLE 4

Effect of Fusion Peptide Analogs on Growth and Viability of Uninfected and HIV-Infected Lymphocytes

| | Cells per ml (% viable) | | | |
|---|---|---|---|---|
| | RH9 | RH9 + PGGP | HIV − RH9 | HIV − RH9 + PGGP |
| Day 1 | 2.6 × 10$^5$ (100) | 2.4 × 10$^5$ (100) | — | — |
| Day 2 | 3.0 × 10$^5$ (100) | 3.2 × 10$^5$ (100) | 1.7 × 10$^5$ (100) | 2.2 × 10$^5$ (100) |
| Day 3 | 1.3 × 10$^6$ (100) | 1.32 × 10$^6$ (100) | — | — |
| Day 4 | 1.2 × 10$^6$ (100) | 1.06 × 10$^6$ (100) | 1.04 × 10$^6$ (95) | 1.12 × 10$^6$ (93) |

What is claimed is:

1. A method for inhibition of a retrovirus which comprises administering to a host a composition comprising an inhibitory effective amount of a peptide of 3 to about 11 amino acids containing the amino acid sequence Phe-X-Gly, wherein X is any amino acid.

2. The method of claim 1 wherein X is selected from the group consisting of phenylalanine, tryptophane, tyrosine, naphthylalanine, alanine, leucine, glycine, valine and isoleucine.

3. The method of claim 2 wherein X is phenylalaine, leucine or glycine.

4. The method of claim 1 wherein the retrovirus is HIV (AIDS) virus.

5. The method of claim 1 wherein the peptide is administered topically.

6. The method of claim 5 wherein the peptide is administered in a composition in the form of a cream, lotion, aqueous solution or suspension, powder, aerosol or suppository.

7. The method of claim 5 wherein the composition has a concentration of about 0.1-10 mM of the peptide.

8. The method of claim 1 wherein the peptide is administered orally or parenterally.

9. The method of claim 8 wherein the peptide is administered in a composition having a concentration of about 0.001-1 mM of the peptide.

10. The method of claim 1 wherein the host is human.

11. The method according to claim 1 wherein the peptide contains from 3 to about 9 amino acids.

12. The method according to claim 1 wherein the peptide is carbobenzoxy-D-Phe-L-Phe-Gly.

13. The method according to claim 1 wherein the peptide is Phe-Gly-Gly-Phe.

* * * * *

UNITED STATES PATENT AND TRADEMARK OFFICE
CERTIFICATE OF CORRECTION

PATENT NO. : 4,880,779
DATED : November 14, 1989
INVENTOR(S) : William R. Gallaher It is certified that error appears in the above-identified patent and that said Letters Patent is hereby corrected as shown below:

Column 7, line 55: "not" should read as --no--

Column 8, line 46: "pprpared" should read as --prepared--

Column 9, line 65: "The" should read as --Two--

Column 10, line 34: "reults" should read as --results--

Column 10, line 36: "x-Phe-Leu" should read as --z-Phe-Leu--

Signed and Sealed this

Seventeenth Day of December, 1991

Attest:

HARRY F. MANBECK, JR.

*Attesting Officer*       *Commissioner of Patents and Trademarks*